US006376460B2

(12) United States Patent
Llewellyn-Smith

(10) Patent No.: US 6,376,460 B2
(45) Date of Patent: Apr. 23, 2002

(54) METHOD OF MODULATING CELLULAR ACTIVITY

(75) Inventor: Ida Jonassen Llewellyn-Smith, Rose Park (AU)

(73) Assignee: Flinders Technologies Pty. Ltd. (AU)

( * ) Notice: Subject to any disclaimer, the term of this patent is extended or adjusted under 35 U.S.C. 154(b) by 0 days.

(21) Appl. No.: 09/369,367

(22) Filed: Aug. 6, 1999

Related U.S. Application Data

(60) Provisional application No. 60/095,655, filed on Aug. 7, 1998.

(51) Int. Cl.$^7$ ................ A01N 61/00; A61K 39/395; A61K 39/40; A61K 34/42; A61K 35/30

(52) U.S. Cl. ............... 514/2; 424/179.1; 424/183.1; 424/570

(58) Field of Search .................... 424/570, 179.1, 424/183.1; 514/2

(56) References Cited

U.S. PATENT DOCUMENTS

| 5,585,348 A | * 12/1996 | Crain et al. |
| 5,989,545 A | * 11/1999 | Foster et al. |

FOREIGN PATENT DOCUMENTS

| WO | WO 96/33273 | * 10/1996 |

OTHER PUBLICATIONS

Wang et al., Neuroscience, 87(1): 275–288. Retrograde and transganglionic transport of horseradish peroxidase–conjugated cholera toxin B subunit, wheatgerm agglutinin and isolectin B4 from Griffonia simplicifolia I in primary afferent neurons innervating, Jan. 1998.*

Seeger et al., J of Neuroscience Research, 48:465–476. Electron microscopic evidence for microglial phagocytic activiry and cholinergic death after administration of the immunotoxin 192IIgG–saporin in rat, Jun. 1997.*

Apartis, E. et al., "Loss of Rhythmically Bursting Neurons in Rat Medial Septum Following Selective Lesion of Septohippocampal Cholinergic System", *The American Physiological Society*, pp. 1633–1642 (1998).

Barbieri, L. et al., "Some Ribosome–Inactivating Proteins Depurinate Ribosomal RNA at Muliple Sites", *Biochem. J.*, vol. 286, pp. 1–4, (1992).

Barbieri, L. et al., "Unexpected Activity of Saporins", *Nature*, vol. 372, p. 624 (Dec. 15, 1994).

Benatti, L. et al., "Nucleotide Sequence of cDNA Coding for Saporin–6, a Type–1 Ribosome–Inactivating Protein from *Saponaria officinalis*", *Eur. J. Biochem.*, vol. 183, pp. 465–470 (1989).

Blessing, W. W. et al., "Destruction of Locus Coeruleus Neuronal Perikarya After Injection of Anti–Dopamine–B–Hydroxylase Immunotix into the Olfactory Bulb of the Rat", *Neuroscience Letters*, vol. 243, pp. 85–88 (1998).

Bolognesi, A. et al., "Induction of Apoptosis by Ribosome–Inactivating Proteins and Related Immunotoxins", *Int. J. Cancer*, vol. 68, pp. 349–355 (1996).

Book, A. et al., "192 IgG–saporin: 1. Specific Lethality of Cholinergic Neurons in the Basal Forebrain of the Rat", *J. of Neuropathology and Experimental Neurology*, vol. 53, No. 1, pp. 95–102 (Jan. 1994).

Book, A. et al., "192 IgG–saporin: 2. Neuropathology in the Rat Brain", *Acta Neuropathol*, vol. 89, pp. 519–526 (1995).

Book, A. et al., "Specificity of 192 IgG–saporin for NGF Receptor–Positive Cholinergic Basal Forebrain Neurons in the Rat", *Brain Research*, vol. 590, pp. 350–355 (1992).

Buechler, Y. et al., "Synthesis and Characterization of a Homogeneous Chemical Conjugate Between Basic Fibroblast Growth Factor and Saporin", *Eur. J. Biochem.*, vol. 234, pp. 706–713 (1995).

Cevolani, D. et al., "Suicide Retrograde Transport of Volkensin in Cerebellar Afferents: Direct Evidence, Neuronal Lesions and Comparison with Ricin", *Brain Research*, vol. 689, pp. 163–171 (1995).

Chessell, I.P. et al., "Selective Loss of Cholinergic Receptors Following Unilateral Intracortical Injection of Volkensin", *Experimental Neurology*, vol. 147, pp. 183–191 (1997).

Davis, T.L. et al., "Anti–Thy–1 Immunotoxin, OX7–Saporin, Destroys Cerebellar Purkinje Cells After Intraventricular Injection in Rats", *Brain Research*, vol. 504, pp. 216–222 (1989).

Engert, A. et al., "A Phase–I Study of an Anti–CD25 Ricin A–Chain Immunotoxin (RFT5–SMPT–dgA) in Patients With Refractory Hodgkin's Lymphoma", *Blood*, vol. 89, No. 2, pp. 403–410 (1997).

Griffiths, G., "The Toxic Plant Proteins Ricin and Abrin Induce Apoptotic Changes in Mammalian Lymphoid Tissues and Intestine", *Journal of Pathology*, vol. 151, pp. 221–229 (1987).

Heath, P.R. et al., "Neuronal Degeneration by Suicide Transport Following Injection of Volkensin into Rat Cerebral Cortex", *Experimental Neurology*, vol. 147, pp. 192–203 (1997).

Heckers, S. et al., "Complete and Selective Cholinergic Denervation of Rat Neocortex and Hippocampus but Not Amygdala by an Immunotoxin Against the p75 NGF Receptor", *Journal of Neuroscience*, vol. 14, No. 3, pp. 1271–1289 (Mar. 1994).

(List continued on next page.)

Primary Examiner—Leon B. Lankford, Jr.
Assistant Examiner—Michele C. Flood
(74) *Attorney, Agent, or Firm*—Merchant & Gould P. C.

(57) ABSTRACT

The present invention is directed to compositions and methods for modulating cellular activity. The invention is particularly suited for delivering an agent which modulates cellular activity to a neuronal cell. In a typical embodiment, a composition of the invention includes an agent associated with a neuronal tracer which associates with a neuron to facilitate uptake of the agent by the neuron cell body.

13 Claims, No Drawings

OTHER PUBLICATIONS

Helke, C.J. et al., "Suicide Transport of Ricin Demonstrates the Presence of Substance P Receptors on Medullary Somatic and Autonomic Motor Neurons", *Brain Research*, vol. 328, pp. 190–195 (1985).

Holley, L. et al., "Cortical Cholinergic Deafferentation Following the Intracortical Infusion of 192 IgG–saporin: A Quantitative Histochemical Study", *Brain Research*, vol. 663, pp. 277–286 (1994).

Ippoliti, R. et al., "A Chimeric Saporin–Transferrin Conjugate Compared to Ricin Toxin: Role of the Carrier in Intracellular Transport and Toxicity", *Research Communication*, pp. 1220–1225 (1995).

Ippoliti, R. et al., "A Ribosomal Protein is Specifically Recognized by Saporin, a Plant Toxin Which Inhibits Protein Synthesis", *FEBS*, vol. 298, No. 2,3, pp. 145–148 (1992).

Ippoliti, R. et al., "The Effect of Monensin and Chloroquine on the Endocytosis and Toxicity of Chimeric Toxins", *CMLS*, vol. 54, pp. 866–875 (1998).

Jouvenceau, A. et al., "Cholinergic Denervation of the Rat Hippocampus by 192–IgG–saporin: Electrophysiological Evidence", *NeuroReport*, vol. 5, pp. 1781–1784 (1994).

Kabat, E. et al., "A Study of the Purification and Properties of Ricin", *J. Biol. Chem.*, vol. 168, pp. 629–639 (1947).

LaRocca, C.D. et al., "Monoclonal anti–Thy 1 Antibody (OX7) is Axonally Transported in Rat Nervous System", *Brain Research*, vol. 449, pp. 381–385 (1988).

Leanza, G. et al., "Effects of Neonatal Lesions of the Basal Forebrain Cholinergic System by 192 Immunoglobulin G–Saporin: Biochemical, Behavioural and Morphological Characterization", *Neuroscience*, vol. 74, No. 1, pp. 119–141 (1996).

Leanza, G. et al., "Extensive and Permanent Motoneuron Loss in the Rat Lumbar Spinal Cord Following Neurotoxic Lesion at Birth: Morphological Evidence", *Neuroscience Letters*, vol. 244, pp. 89–92 (1998).

Leanza, G. et al., "Selective Lesioning of the Basal Forebrain Cholinergic System by Intraventricular 192 IgG–saporin: Behavioural, Biochemical and Stereological Studies in the Rat", *European Journal of Neuroscience*, vol. 7, pp. 329–343 (1995).

Lin, J. et al., "Abrin and Ricin: New Anti–tumour Substances", *Nature*, vol. 227, pp. 292–293 (Jul. 18, 1970).

Lin, J. et al., "Effect of Crystalline Ricin on the Biosynthesis of Protein, RNA, and DNA in Experimental Tumor Cells", *Cancer Research*, vol. 31, No. 7, pp. 921–923 (Jul. 1971).

Lin, L. et al., "Cognitive Changes and Modified Processing of Amyloid Precursor Protein in the Cortical and Hippocampal System After Cholinergic Synapse Loss and Muscarine Receptor Activation", *PNAS*, vol. 96, pp. 12108–12113 (Oct. 12, 1999).

Lynch, T. et al., "Immunotoxin Therapy of Small–Cell Lung Cancer: A Phase I Study of N901–Blocked Ricin", *Journal of Clinical Oncology*, vol. 15, No. 2, pp. 723–734 (Feb. 1997).

Madden, C. et al., "Lesions of the C1 Catecholaminergic Neurons of the Ventrolateral Medulla in Rats Using Anti–DβH–saporin", *American Physiological Society*, pp. R1063–R1075 (1999).

Mantyh, P. et al., "Inhibition of Hyperalgesia by Ablation of Lamina I Spinal Neurons Expressing the Substance P Receptor", *Science*, vol. 278, pp. 275–279 (Oct. 10, 1997).

Maras, B. et al., "The Amino Acid Sequence of a Ribosome–Inactivating Protein From *Saponaria officinalis* Seeds", *Biochemistry International*, vol. 21, No. 5, pp. 831–838 (Aug. 1990).

Martin, W. et al., "Differential Effects of Neurotoxic Destruction of Descending Noradrenergic Pathways on Acute and Persistent Nociceptive Processing", *Pain*, vol. 80, pp. 57–65 (1999).

Milner, T. et al., "Septal Cholinergic Deafferentation of the Dentate Gyrus Results in a Loss of a Subset of Neuropeptide Y Somata an Increase in Synaptic Area on Remaining Neuropeptide Y Dendrites", *Brain Research*, vol. 831, pp. 322–336 (1999).

Moolten, F. et al., "Immunotheraphy of Experimental Animal Tumors With Antitumor Antibodies Conjugated to Diphtheria Toxin or Ricin", *Annals New York Academy of Sciences*, vol. 217, pp. 690–699 (1976).

Oeltmann, T. et al., "A Hybrid Protein Containing the Toxic Subunit of Ricin and the Cell–specific Subunit of Human Chlorionic Gonadotropin", *Journal of Biological Chemistry*, vol. 254, No. 4, pp. 1028–1032 (1979).

Ohtake, T. et al., "Retrograde Degeneration and Colchicine Protection of Basal Forebrain Cholinergic Neurons Following Hippocampal Injections of An Immunotoxin Against the P75 Nerve Growth Factor Receptor", *Neuroscience*, vol. 78, No. 1, pp. 123–133 (1997).

Pallera, A. et al., "192 IgG–Saporin Causes a Major Loss of Synaptic Content in Rat Olfactory Bulb", *Experimental Neurology*, vol. 127, pp. 265–277 (1994).

Pappas, B.A. et al., "192 IgG–saporin Lesion of Basal Forebrain Cholinergic Neurons in Neonatal Rats", *Developmental Brain Research*, vol. 96, pp. 52–61 (1996).

Picklo, M. et al., "Anti–Dopamine β–Hydroxylase Immunotoxin–Induced Sympathectomy in Adult Rats", *Journal of Pharmacology and Experimental Therapeutics*, vol. 275, No. 2, pp. 1003–1010 (1995).

Picklo, M. et al., "Noradrenergic Lesioning with an Anti–Dopamine β–Hydroxylase Immunotoxin", *Brain Research*, vol. 666, pp. 195–200 (1994).

Ridley, R. et al., "Severe Learning Impairment Caused by Combined Immunotoxic Lesion of the Cholinergic Projections to the Cortex and Hippocampus in Monkeys", *Brain Research*, vol. 836, pp. 120–138 (1999).

Roberts, R. et al., "Differential Effects of Suicide Transport Lesions of the Striatonigral or Striatopallidal Pathways on Subsets of Striatal Neurons", *Experimental Neurology*, vol. 124, pp. 242–252 (1993).

Roberts, R. et al., "Effects of Suicide Transport Lesions of the Striatopallidal or Striatonigral Pathways on Striatal Ultrastructure", *Brain Research*, vol. 701, pp. 227–237 (1995).

Robertson, R. et al., "Neonatal Treatment with 192 IgG–Saporin Produces Long–term Forebrain Cholinergic Deficits and Reduces Dendritic Branching and Spine Density of Neocortical Pyramidal Neurons", *Cerebral Cortex*, vol. 8, pp. 142–155 (Mar. 1998).

Roβner, S. et al., "192 IgG–Saporin Immunotoxin–Induced Loss of Cholinergic Cells Differentially Activates Microglia in Rat Basal Forebrain Nuclei", *Journal of Neuroscience Research*, vol. 41, pp. 335–346 (1995).

Roβner, S. et al., "192 IgG–Saporin–Induced Immunotoxic Lesions of Chloinergic Basal Forebrain System Differentially Affect Glutamatergic and GABAergic Markers in Cortical Rat Brain Regions", *Brains Research*, vol. 696, pp. 165–176 (1995).

Roβner, S. et al., "Differential Changes in Cholinergic Markers From Selected Brain Regions After Specific Immunolesion of the Rat Cholinergic Basal Forebrain System", *Journal of Neuroscience Research*, vol. 40, pp. 31–43 (1995).

Roβner, S. et al., "Differential Expression of Immediate Early Genes in Distinct Layers of Rat Cerebral Cortex After Selective Immunolesion of the Forebrain Cholinergic System", *Journal of Neuroscience Research*, vol. 38, pp. 282–293 (1994).

Salo, P. et al., "Selective Ablation of Rat Knee Joint Innervation with Injected Immunotoxin: A Potential New Model for the Study of Neuropathic Arthritis", *Journal of Orthopaedic Research*, vol. 15, pp. 622–628 (1997).

Schreihofer, A.M. et al., "Abolition of Cyanide–Induced Sympathoexcitation by Selective Lesion of Bulbospinal (BS) Catecholaminergic (CA) Neurons", *Soc. Neurosci. Abstr.*, vol. 25, p. 1173 (1999).

Siena, S. et al., "Synthesis and Characterization of an Antihuman T–Lymphocyte Saporin Immunotoxin (OKT1–SAP) with in vivo Stability into Nonhuman Primates", *Blood*, vol. 72, No. 2, pp. 756–765 (Aug. 1988).

Sperti, S. et al., "Inhibition by Ricin of Protein Synthesis in vitro: 60 S Ribosomal Subunit as the Target of the Toxin", *Biochem. J.*, vol. 136, pp. 813–815 (1973).

Stirpe, F. et al., "Modification of Ribosomal RNA by Ribosome–Inactivating Proteins from Plants", *Nucleic Acids Research*, vol. 16, No. 4, pp. 1349–1357 (1988).

Stirpe, F. et al., "Ribosome–inactivating Proteins from the Seeds of *Saponaria officinalis* L. (soapwort), of *Agrostemma githago* L. (corn cockle) and of *Asparagus officinalis* L. (asparagus), and from the Latex of *Hura crepitans* L. (sandbox tree)", *Biochem. J.*, vol. 216, pp. 617–625 (1983).

Streit, W. et al., "Response of Endogenous Glial Cells to Motor Neuron Degeneration Induced by Toxic Ricin", *Journal of Comparative Neurology*, vol. 268, pp. 248–263 (1988).

Tang, H.Z. et al., "Selective Inhibition of Neuronal Protein Synthesis by Retrogradely Transported Ricin", *Journal of Neuroscience Methods*, vol. 55, pp. 15–22 (1994).

Tazzari, P. et al., "Ber–H2 (anti–CD30)–Saporin Immunotoxin: A New Tool for the Treatment of Hodgkin's Disease and CD30+ Lumphoma: in vitro Evaluation", *British Journal of Haematology*, vol. 81, pp. 203–211 (1992).

Thorpe, P. et al., "An Immunotoxin Composed of Monoclonal Anti–Thy 1.1 Antibody and a Ribosome–Inactivating Protein from *Saponaria officinalis*: Potent Antitumor Effects In Vitro and In Vivo", *JNCI*, vol. 75, No. 1, pp. 151–159 (Jul. 1985).

Thorpe, P. et al., "Cytotoxicity Acquired by Conjugation of an Anti–Thy$_{1.1}$ Monoclonal Antibody and the Ribosome–Inactivating Protein, Gelonin", *Eur. J. Biochem.*, vol. 116, pp. 447–454 (1981).

Thorpe, P. et al., "The Preparation and Cytotoxic Properties of Antibody–Toxin Conjugates", *Immunological Rev.*, vol. 62, pp. 119–158 (1982).

Torres, E.M. et al., "Behavioural, Histochemical and Biochemical Consequences of Selective Immunolesions in Discrete Regions of the Basal Forebrain Cholinergic System", *Neuroscience*, vol. 63, No. 1, pp. 95–122 (1994).

Vulchanova, L. et al., "Depletion of IB4–Binding Sensory Neurons Results in Elevated Nociceptive Thresholds", *Soc. Neurosci. Abstr.*, vol. 25, p. 684 (1999).

Waite, J.J. et al., "192 Immunoglobulin G–Saporin Produces Graded Behavioral and Biochemical Changes Accompanying the Loss of Cholinergic Neurons of the Basal Forebrain and Cerebellar Purkinje Cells", *Neuroscience*, vol. 65, No. 2, pp. 463–476 (1995).

Waite, J.J. et al., "Time Course of Cholinergic and Monoaminergic Changes in Rat Brain After Immunolesioning with 192 IgG–Saporin", *Neuroscience Letters*, vol. 169, pp. 154–158 (1994).

Wall, J.T. et al., "Cortical Organization After Treatment of a Peripheral Nerve With Ricin: An Evaluation of the Relationship Between Sensory Neuron Death and Cortical Adjustments After Nerve Injury", *The Journal of Comparative Neurology*, vol. 277, pp. 578–592 (1988).

Walsh, T.J., et al., "Behavioral and Neurobiological Alterations Induced by the Immunotoxin 192–IgG–Saporin: Cholinergic and Non–Cholinergic Effects Following i.c.v. Injection", *Brain Research*, vol. 702, pp. 233–245 (1995).

Wenk, G. et al., "Behavioral, Biochemical, Histological, and Electrophysiological Effects of 192 IgG–Saporin Injections into the Basal Forebrain of Rats", *Journal of Neuroscience*, vol. 14, No. 10, pp. 5986–5995 (Oct. 1994).

Wiley, R.G. et al., "Destruction of Neurokinin–1 Receptor Expressing Cells In Vitro and In Vivo Using Substance P–Saporin in Rats", *Neuroscience Letters*, vol. 230, pp. 97–100 (1997).

Wiley, R.G. et al., "Destruction of the Cholinergic Basal Forebrain Using Immunotoxin to Rat NGF Receptor: Modeling the Cholinergic Degeneration of Alzheimer's Disease", *Journal of the Neurological Sciences*, vol. 128, pp. 157–166 (1995).

Wiley, R.G. et al., "Immunolesioning: Selective Destruction of Neurons Using Immunotoxin to Rat NGF Receptor", *Brain Research*, vol. 562, pp. 149–153 (1991).

Wiley, R.G. et al., "Modeccin and Volkensin but not Abrin are Effective Suicide Transport Agents in Rat CNS", *Brain Research*, vol. 438, pp. 145–154 (1988).

Wiley, R.G. et al., "Neural Lesioning with Ribosome–Inactivating Proteins: Suicide Transport and Immunolesioning", *TINS*, vol. 15, No. 5, pp. 285–290 (1992).

Wiley, R.G. et al., "Neuronotoxic Effects of Monoclonal Anti–Thy 1 Antibody (OX7) Coupled to the Ribosome Inactivating Protein, Saporin, as Studied by Suicide Transport Experiments in the Rat", *Brain Research*, vol. 505, pp. 44–54 (1989).

Wiley, R.G. et al., "Ricin Transport Distinguishes Between Central and Peripheral Neurons", *Brain Research*, vol. 269, pp. 357–360 (1983).

Wiley, R.G. et al., "Suicide Transport: Destruction of Neurons by Retrograde Transport of Ricin, Abrin, and Modeccin", *Science*, vol. 216, pp. 889–890 (May 1982).

Wiley, R.G. et al., "Targeting Toxins to Neural Antigens and Receptors", *Seminars in Cancer Biology*, vol. 7, pp. 71–77 (1996).

Yu, J. et al., "Altered NGF Protein Levels in Different Brain Areas After Immunolesion", *Journal of Neuroscience Research*, vol. 43, pp. 213–223 (1996).

Yu, C. et al., "The Biologic Effects of Growth Factor–Toxin Conjugates in Models of Vascular Injury Depend on Dose, Mode of Delivery, and Animal Species", *Journal of Pharmaceutical Sciences*, vol. 87, No. 11, pp. 1300–1304 (Nov. 1998).

\* cited by examiner

METHOD OF MODULATING CELLULAR ACTIVITY

The present invention claims priority to U.S. Provisional Application Ser. No. 60/095,655, filed Aug. 7, 1998, the entire disclosure of which is incorporated herein by reference.

Field of the Invention

The present invention relates generally to a method of modulating neuron cellular activity and agents useful for same. More particularly, the present invention contemplates inducing the apoptosis of neurons. Even more particularly, the present invention provides a method of inducing the apoptosis of specific sub-populations of neurons by administering an apoptosis inducing agent fused, linked or otherwise associated with a neuronal tracer. The method of the invention is useful, inter alia, in a variety of therapeutic or prophylactic applications.

BACKGROUND OF THE INVENTION

Bibliographic details of the publications numerically referred to in this application are collected at the end of the description.

Throughout this specification and the claims which follow, unless the context requires otherwise, the word "comprise", and variations such as "comprises" and "comprising", will be understood to imply the inclusion of a stated integer or step or groups of integers or steps but not the exclusion of any other integer or step or group of integers or steps.

Identifying "magic bullets", chemicals that will cure disease without causing major side effects, has always been a major goal of clinical medicine. One avenue for producing magic bullets for a variety of diseases was opened by the purification of ricin from castor oil seeds. Kabat E E, et al., *J. Biol. Chem.,* 168:629 (1947). Ricin destroys a cell's ability to make proteins by binding to and inactivating ribosomes, an essential component of the cell's protein synthetic machinery. Lin J Y, et al., *Cancer Res.* 31:921 (1971); Sperti S, et al., *Biochem J.,* 136:813 (1973). Because the cell cannot make protein, it dies over hours to days through apoptotic mechanisms. Bolognesi, et al., *Int. J. Center.,* 68:349 (1996). Ribosomal inactivating proteins (RIP's) with a similar activity to ricin have been isolated from a number of different plants (for example, abrin, saporin, modeccin). Although it was shown as early as 1970 that ricin was capable of killing tumor cells, RIP's were not immediately enlisted for therapeutic use in humans. Lin J-Y, et al., *Nature,* 227:292 (1970). The problem was one of targeting and specificity. RIP's could be internalized by many different kinds of cells and were often lethal to animals at low doses.

A major step toward the application of RIP's to the treatment of human disease came with the linking of ricin molecules that allowed the toxin to be targeted to a precisely defined population of cells in the body. The first agents used to target RIP's were antibodies that recognized and bound to proteins on certain types of cancer cells. Moolten F, et al., *Ann. N.Y. Acad. Sci.,* 277:690 (1976). Ligands that bound to specific types of cell surface receptors were also rapidly adopted as a means of getting RIP's into cells. Oeltmann T N, et al., *J. Clin. Oncol.,* 254:1028 (1979). These advances led to an explosion in the investigation of the uses of cell type—specific toxins based on the RIP's, ricin and saporin; and human trials have already occurred by antibody—linked RIP's (immunotoxins") designed to eliminate certain types of cancer cell. See e.g., Lynch T J Jr, et al., *J. Clin. Oncol.,* 15:723 (1997); Engert A, et al., *Blood,* 89:403 (1997).

Treatment or cure of neurological problems that are caused by permanent dysfunction or excessive activation of populations of nerve cells are goals for RIP therapy. For these types of problems, drug treatments and surgery often provide only partial or transient solutions. For example, intramuscular injections of botulinum toxin, which are used to treat disorders characterized by involuntary muscle spasms, work for only a short time and muscle fibers eventually become resistant to the action of the toxin. Treatment of chronic pain often involves pain-killing drugs that become decreasingly effective with time and requires surgery to implant catheters to deliver the drugs directly into the space around the spinal cord. In these cases, as in many others, killing the dysfunctional or overactive nerve cells could permanently relieve or cure the clinical problem.

Despite the therapeutic appeal of killing nerve cells, RIP's have not been extensively assessed for their clinical potential in neurology. The reasons for this include the types of nerve cells that can currently be specifically and selectively killed by RIP-based neurotoxins and their methods of delivery. Ricin injected into the blood stream has been shown to kill nerve cells that lie outside the central nervous system, Wiley RG, et al., *Brain Res.,* 438:148 (1983), but not central neurons; and, when injected into the brain, ricin causes non-specific damage, killing large numbers of neurons at the site where it is injected. See e.g., Health PR, et al., *Exp. Neurol.,* 147:192 (1997).

To achieve more precise targeting of RIP-based neurotoxins, antibodies that recognize proteins on the surfaces of nerve cells have been linked to saporin and these immunotoxins have been shown to eliminate specific subsets of brain neurons. Effective immunoneurotoxins include saporin linked to an antibody directed against the low affinity receptor for nerve growth factor (IgG192-saporin) which kills central cholinergic neurons, Book AA, et al., *Brain Res.,* 590:350 (1992), and saporin linked to anti-dopamine β-hydroxylase, an enzyme required for the synthesis of some catacholamine neurotransmitters which kills noradrenergic neurons. Picklo M J, et al., *Brain Res.,* 195 (1994).

Neurotoxins have also been made from saporin and ligands that bind to specific types of receptors that occur on nerve cells, such as Substance P-saporin, which binds to the neurokinin-1 receptor and kills a subset of dorsal horn neurons involved in processing information about painful stimuli. Mantyh P W, et al., *Science.* 278:275 (1997).

Currently, immunoneurotoxins and receptor ligand-based neurotoxins must be either injected directly into brain tissue or introduced into the ventricles of the brain or the intrathecal space around the spinal cord so that the toxin can gain access to the susceptible nerve cells via the cerebrospinal fluid.

Accordingly, there is a need to expand the currently limited accessibility of neurotoxin therapy to populations of neurons. For example, the range of currently accessible neuron types needs to be expanded to include a larger range of clinically relevant cell types. Further, there is a need to develop less invasive methods for exposing neurons to neurotoxic agents.

SUMMARY OF THE INVENTION

The present invention is directed to methods for delivering neurotoxins to neurons. The methods include the utilization of retrograde neuronal tracers which permit access to an expanded range of neuron types, via the periphery, which is a less invasive route of administration. Further, the use of neuron tracers also permits the delivery of neurotoxins to selective sub-populations of neurons.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

One aspect of the invention provides a method of modulating neuron cellular activity in a subject comprising administering to the subject an effective amount of an agent linked, fused or otherwise associated with a neuronal tracer wherein the tracer links, fuses or otherwise associates with the neuron and facilitates the transportation of the agent to the cell body of the neuron whereby the agent can modulate the cellular activity of the neuron.

Another aspect of the invention provides a method of modulating neuron cellular activity in a subject, comprising peripherally administering to the subject an effective amount of an agent linked, fused or otherwise associated with a neuronal tracer wherein the tracer links, fuses or otherwise associates with the neuron and facilitates the transportation of the agent to the cell body of the neuron whereby the agent modulates the cellular activity of the neuron.

Yet another aspect of the invention provides a method of modulating neuron cellular activity in a subject comprising peripherally administering to the subject an effective amount of an agent linked, fused or otherwise associated with a retrograde neuronal tracer wherein the retrograde neuronal tracer links, fuses or otherwise associates with the neuron and facilitates the transportation of the agent to the cell body of the neuron whereby the agent modulates the cellular activity of the neuron.

A further aspect of the invention provides a method of inducing neuron apoptosis in a subject comprising peripherally administering to the subject an effective amount of an apoptosis inducing agent linked, fused or otherwise associated with a retrograde neuronal tracer wherein the tracer links, fuses or otherwise associates with the neuron and facilitates the transportation of the agent to the cell body of the neuron whereby the agent induces the apoptosis of the neuron.

Still a further aspect of the invention provides a method of inducing neuron apoptosis in a subject comprising peripherally administering to the subject an effective amount of a neurotoxin or derivative thereof linked, fused or otherwise associated with a cholera toxin B subunit tracer wherein the tracer links, fuses or otherwise associates with the neuron and facilitates the transportation of the neurotoxin to the cell body of the neuron whereby the neurotoxin induces the apoptosis of the neuron.

Another aspect of the invention provides a method of delivering to the cell body of a neuron, an agent capable of modulating neuron cellular activity in a subject comprising administering to the subject an effective amount of an agent capable of modulating the cellular activity of a neuron the agent being linked, fused or otherwise associated with a neuronal tracer wherein the tracer links, fuses or otherwise associates with the neuron and facilitates the transportation of the agent to the cell body of the neuron.

Still another aspect of the invention provides a method of delivering to the cell body of a neuron, via the periphery, an agent capable of modulating neuron cellular activity in a subject comprising peripherally administering to the subject an effective amount of an agent capable of modulating the cellular activity of a neuron the agent being linked, fused or otherwise associated with a neuronal tracer wherein the tracer links, fuses or otherwise associates with the neuron and facilitates the transportation of the agent to the cell body of the neuron.

Still yet another aspect of the present invention provides a method of delivering saporin, via the periphery, to the cell body of a neuron in a subject comprising peripherally administering to the subject an effective amount of saporin linked, fused or otherwise associated with a cholera toxin B subunit wherein the cholera toxin B subunit links, fuses or otherwise associates with the neuron and facilitates the transportation of the saporin to the cell body of the neuron whereby the saporin induces the apoptosis of the neuron.

A further aspect of the invention relates to a method of treatment or prophylaxis of a disease condition in a subject comprising administering to the subject an effective amount of an agent linked, fused or otherwise associated with a neuronal tracer for a time and under conditions sufficient for the tracer to link, fuse or otherwise associate with the neuron and facilitate the transportation of the agent to the cell body of the neuron whereby the agent modulates the cellular activity of the neuron.

Still a further aspect of the present invention relates to a method of treatment or prophylaxis of a disease condition involving involuntary muscle spasms or chronic pain comprising administering to a subject an effective amount of an agent linked, fused or otherwise associated with a neuronal tracer for a time and under conditions sufficient for the tracer to link, fuse or otherwise associate with the neuron and facilitate the transportation of the agent to the cell body of the neuron whereby the agent modulates the cellular activity of the neuron.

In yet another further aspect of the invention there is provided a method of treatment or prophylaxis of a disease condition involving involuntary muscle spasms or chronic pain in a subject comprising peripherally administering to the subject an effective amount of an agent capable of inducing apoptosis of a neuron the agent being linked, fused or otherwise associated with a retrograde neuronal tracer for a time and under conditions sufficient for the tracer to link, fuse or otherwise associate with the neuron and facilitate the transportation of the agent to the cell body of the neuron whereby the agent induces the apoptosis of the neuron.

Yet another aspect the invention relates to the use of a composition comprising an agent capable of modulating neuronal cell activity linked, fused or otherwise associated with a neuronal tracer in the manufacture of a medicament for the modulation of neuronal cell activity in a subject.

Another aspect of the present invention provides a composition for use in modulating the cellular activity of a neuron comprising an agent linked fused or otherwise associated with a neuronal tracer and one or more pharmaceutically acceptable carriers and/or diluents.

DETAILED DESCRIPTION OF THE INVENTION

The method of the present invention is predicated, in part, on the elucidation of an intracellular neuron transportation mechanism which utilizes retrograde neuronal tracers and thereby permits the delivery of molecules, which act upon the neuron cell body, via the peripheral regions of a neuron's cellular processes. The elucidation of this transportation mechanism now permits the development of methods of treating neural disorders which require the delivery of modulatory agents to the cell bodies of a population of neurons.

One aspect of the present invention provides a method of modulating neuron cellular activity in a subject the method comprising administering to the subject an effective amount of an agent associated with (i.e., linked, fused or otherwise associated with) a neuronal tracer wherein the tracer associates with (i.e., links, fuses or otherwise associates with) the neuron and facilitates the transportation of the agent to the cell body of the neuron whereby the agent modulates the cellular activity of the neuron.

The term "subject" should be understood to include humans, primates, livestock animals (eg. horses, cattle, sheep, pigs, donkeys), laboratory test animals (eg. mice, rats, rabbits, guinea pigs), companion animals (eg. dogs and cats) and captive wild animals (eg. kangaroos, deer, foxes,), aves (eg. chickens, ducks, emus), reptiles, amphibians and fish. Typically, the subject is a human or a laboratory test animal.

Reference to "neuron" should be understood in its broadest sense to include reference to any cell which transmits nerve impulses. This includes, but is not limited to, neurons of the central and peripheral nervous systems, which include the autonomic nervous system (which comprises the sympathetic and parasympathetic nervous systems). A neuron is typically, but not necessarily, composed of a cell body from which extends dendrites and an axon. Accordingly, reference to a "cell body" should be understood as a reference to the region of a neuron from which the dendrites and axon radiate. The cell body contains the nucleus of a neuron. Examples of neurons include pain sensing neurons and motor neurons, which comprise the nerve pathway between the brain and an effector organ such as a skeletal muscle.

The present invention is predicated on the use of neuronal tracers which link, fuse or otherwise associate with the cell membrane of a neuron or a molecule associated with the cell membrane, such as a molecule anchored to the cell membrane or comprising a transmembrane region, thereby permitting delivery to the cell body of the neuron of any agent linked, fused or otherwise associated with the neuronal tracer. Whereas prior to the advent of the present invention, agents, such as neurotoxins, were delivered to neurons either by injection directly into brain tissue or the intrathecal space around the spinal cord. The method of the present invention now permits delivery of those agents via any region of a subject's body into which neuronal axons or dendrites extend. For example, the cell body of motor neurons, the axons of which innervate muscles, can now be accessed by agents which are delivered via an intramuscular injection.

Accordingly, the present invention more particularly provides a method of modulating neuron cellular activity in a subject comprising peripherally administering to the subject an effective amount of an agent linked, fused or otherwise associated with a neuronal tracer wherein the tracer links, fuses or otherwise associates with the neuron and facilitates the transportation of the agent to the cell body of the neuron whereby the agent modulates the cellular activity of the neuron.

Reference to "periphery" should be understood as a reference to any region of the subject's body other than the central nervous system. It should be understood that the method of the present invention is particularly directed to accessing neurons via the periphery irrespective of whether the cell body region of the neuron is located within or outside the central nervous system. Reference to "peripherally administering" should be understood as administration of an agent at a peripheral region of the subject's body.

Reference to a "neuronal tracer" should be understood as a reference to a proteinaceous or non-proteinaceous molecule which associates with a neuron, thereby facilitating uptake of the agent, such as an agent capable of modulating the cellular activity of a neuron coupled to the tracer by the neuron. The neuronal tracer may bind to any component of the neuron including, but not limited to, the cell membrane or molecules anchored to the cell membrane such as gangliosides or cell surface receptors. The neuronal tracer may bind at any point along the cell membrane including, for example, at any point along a dendrite or axon or at the cell body. Neuronal tracers may bind non-specifically to any type of neuron or may bind specifically to certain membrane anchored molecules thereby facilitating the delivery of an agent to specific sub-populations of neurons expressing the specific membrane anchored molecules.

Preferably, the neuronal tracer is a retrograde neuronal tracer. Reference to a "retrograde" neuronal tracer should be understood as a reference to a neuronal tracer which is retrogradely transported from any point along a neuronal cell process, such as a dendrite or an axon, to the neuron cell body.

Without limiting the present invention to any one theory or mode of action, retrograde transport is effected through specific and selective binding of a retrograde neuronal tracer to a component of the neuron membrane. The retrograde neuronal tracer, which is associated with an agent such as an agent capable of modulating cellular activity of a neuron, binds to the specific component which is associated with the cell membrane of the neuron, it is internalized and thereafter facilitates the transport of the agent from the point of internalization to the neuron cell body where the agent acts to modulate the cellular activity of the neuron. Reference to "facilitating the transportation" of the agent should be understood as a reference to the tracer either directly or indirectly acting to induce transportation of the agent to the cell body. The agent may be transported either in isolation or while still complexed to the tracer. For example, a retrograde tracer, complexed to an agent, which is administered intramuscularly, may bind to the peripheral region of the axon of a motor neuron wherein it is internalized and facilitates transportation of the agent along the axon to the motor neuron cell body where the agent directly or indirectly modulates the cellular activity of the neuron. Examples of retrograde neuronal tracers include, but are not limited to, cholera toxin B subunit, wheat germ agglutinin and isolectin B4 from *Bandeireaea simplicifolia.*

Accordingly, the present invention more particularly provides a method of modulating neuron cellular activity in a subject comprising peripherally administering to the subject an effective amount of an agent linked, fused or otherwise associated with a retrograde neuronal tracer wherein the retrograde tracer links, fuses or otherwise associates with the neuron and facilitates the transportation of the agent to the cell body of the neuron whereby the agent modulates the cellular activity of the neuron.

Preferably the retrograde neuronal tracer is cholera toxin B subunit, wheat germ agglutinin or isolectin B4 from *Bandeireaea simplicifolia* and most preferably cholera toxin B subunit. The association may be achieved by any mechanism including, but not limited to, linking via a peptide bond, ionic bond, hydrogen bond, covalent bond, van Der Waals forces or other interactive bonding mechanism.

Reference to "modulation of neuron cellular activity" should be understood as a reference to the up and down-regulation of any one or more activities which a neuron is capable of performing such as, but not limited to, any one or more of maintenance of neuron viability, differentiation, cell signaling mechanisms, cell surface molecule expression or cytokine production. Preferably the modulation of functional activity is down-regulation of the maintenance of neuron viability and most preferably the induction of neuron cell death either by the delivery of a lethal hit or the induction of neuron apoptosis.

Accordingly, the present invention provides a method of inducing neuron apoptosis in a subject comprising peripherally administering to the subject an effective amount of an apoptosis inducing agent linked, fused or otherwise associated with a retrograde neuronal tracer wherein the tracer links, fuses or otherwise associates with the neuron and facilitates the transportation of the agent to the cell body of the neuron whereby the agent induces the apoptosis of the neuron.

References to an "agent" should be understood as a reference to any proteinaceous or non-proteinaceous molecule which directly or indirectly modulates the cellular activity of a neuron and, in particular, induces the apoptosis of a neuron. The proteinaceous molecule may be derived from natural or recombinant sources including fusion proteins or following, for example, natural product screening. The non-proteinaceous molecule may be derived from natural sources, such as for example natural product screening or may be chemically synthesized. For example, agents capable of directly or indirectly inducing apoptosis of a neuron including neurotoxins such as ricin or ribosomal inactivating proteins such as abrin, saporin or modeccin and derivatives thereof.

Accordingly, in a preferred embodiment, the present invention provides a method of inducing neuron apoptosis in a subject comprising peripherally administering to the subject an effective amount of a neurotoxin or derivative thereof linked, fused or otherwise associated with a cholera toxin B subunit tracer wherein the tracer links, fuses or otherwise associates with the neuron and facilitates the transportation of the neurotoxin to the cell body of the neuron whereby the neurotoxin induces the apoptosis of the neuron. Preferably the neurotoxin is a ribosomal inactivating protein or derivative thereof and even more preferably saporin.

An "effective amount" means an amount necessary to at least partly obtain the desired response. This amount varies depending upon the health and physical condition of the individual to be treated, the taxonomic group of the individual to be treated, the assessment of the medical situation and other relevant factors. It is expected that the amount will fall within a relatively broad range that can be determined through routine trials.

The term "derivatives" as used herein includes but is not limited to fragments, homologues, analogues, mutants, mimetics and variants thereof. This includes homologues, analogues, mutants, mimetics and variants derived from natural or recombinant resources including fusion proteins.

The homologues, analogues, mutants, variants and mimetics may be derived from insertion, deletion or substitution of amino acids in the components. Amino acid insertional derivatives of the components used in the present invention include amino and/or carboxylic terminal fusion as well as intra-sequence insertions of single or multiple amino acids. Insertional amino acid sequence variants are those in which one or more amino acid residues are introduced into a predetermined site in the protein although random insertion is also possible with suitable screening of the resulting product. Deletional variants are characterized by the removal of one or more amino acids from the sequence. Substitutional amino acid variants are those in which at least one residue in the sequence has been removed from a different residue inserted in its place. Typical substitutions are those made in accordance with Table 1:

TABLE 1

Suitable residues for amino acid substitutions

| Original Residue | Exemplary Substitutions |
|---|---|
| Ala | Ser |
| Arg | Lys |
| Asn | Gln; His |
| Asp | Glu |
| Cys | Ser |
| Gln | Asn |
| Glu | Ala |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Additions" to amino acid sequences or nucleotide sequences include fusions with other peptides, polypeptides.

Yet another aspect of the present invention provides a method of delivering to the cell body of a neuron an agent capable of modulating neuron cellular activity in a subject comprising administering to the subject an effective amount of an agent capable of modulating the cellular activity of a neuron the agent being linked, fused or otherwise associated with a neuronal tracer wherein the tracer links, fuses or otherwise associates with the neuron and facilitates the transportation of the agent to the cell body of the neuron.

More particularly, the present invention provides a method of delivering to the cell body of a neuron, via the periphery, an agent capable of modulating neuron cellular activity in a subject comprising peripherally administering to the subject an effective amount of an agent capable of modulating the cellular activity of a neuron the agent being linked, fused or otherwise associated with a neuronal tracer wherein the tracer links, fuses or otherwise associates with the neuron and facilitates the transportation of the agent to the cell body of the neuron.

Preferably the modulation of cellular activity is the induction of neuron apoptosis. Even more preferably the agent is a neurotoxin such as saporin and the neuronal tracer is a retrograde neuronal tracer such as cholera toxin B subunit.

According to this preferred embodiment of the present invention, there is provided a method of delivering saporin, via the periphery, to the cell body of a neuron in a subject comprising peripherally administering to the subject an effective amount of saporin linked, fused or otherwise associated with a cholera toxin B subunit wherein the cholera toxin B subunit links, fuses or otherwise associates with the neuron and facilitates the transportation of the saporin to the cell body of the neuron whereby the saporin induces the apoptosis of the neuron.

The present invention is useful in relation to disease conditions. For example, the method of the present invention as hereinbefore defined is particularly useful, but in no way limited to, use as a prophylactic or as a therapy in relation to disease conditions which involve permanent disfunction or excessive activation of populations of neural cells such as disorders characterized by involuntary muscle spasms and chronic pain.

Accordingly, another aspect of the present invention relates to a method of treatment or prophylaxis of a disease condition in a subject comprising administering to the subject an effective amount of an agent linked, fused or otherwise associated with a neuronal tracer for a time and under conditions sufficient for the tracer to link, fuse or otherwise associate with the neuron and facilitate the transportation of the agent to the cell body of the neuron whereby the agent modulates the cellular activity of the neuron.

More particularly the present invention relates to a method of treatment or prophylaxis of a disease condition involving involuntary muscle spasms or chronic pain comprising administering to a subject an effective amount of an agent linked, fused or otherwise associated with a neuronal tracer for a time and under conditions sufficient for the tracer to link, fuse or otherwise associate with the neuron and facilitate the transportation of the agent to the cell body of the neuron whereby the agent modulates the cellular activity of the neuron.

Preferably the administration is peripheral administration, the neuronal tracer is a retrograde neural tracer and the modulation of neuron cellular activity is the induction of neuron apoptosis.

According to this preferred embodiment there is provided a method of treatment or prophylaxis of a disease condition involving involuntary muscle spasms or chronic pain in a subject comprising peripherally administering to the subject an effective amount of an agent capable of inducing apoptosis of a neuron the agent being linked, fused or otherwise associated with a retrograde neuronal tracer for a time and under conditions sufficient for the tracer to link, fuse or otherwise associate with the neuron and facilitate the transportation of the agent to the cell body of the neuron whereby the agent induces the apoptosis of the neuron.

Preferably the agent is a neurotoxin and more preferably saporin or derivative thereof. Still more preferably the retrograde neuronal tracer is cholera toxin B subunit or derivative thereof.

It is envisaged that the method of the present invention may be utilized, for example, for the localized injection of a neurotoxin tracer complex to kill only a proportion of the neurons which send axons to a given target.

Administration of the agent and neuronal tracer complex or derivative thereof, in the form of a pharmaceutical composition, may be performed by any convenient means. The agent or component or functional equivalent thereof of the pharmaceutical composition is contemplated to exhibit therapeutic activity when administered in an amount which depends on the particular case. The variation depends, for example, on the human or animal and the agent chosen. A broad range of doses may be applicable. Considering a patient, for example, from about 0.1 mg to about 1 mg of the agent or component or functional equivalent thereof may be administered per kilogram of body weight per day. Dosage regimes may be adjusted to provide the optimum therapeutic response. For example, several divided doses may be administered daily, weekly, monthly or at other suitable time intervals or the dose may be proportionally reduced as indicated by the exigencies of the situation. The agent or component or functional equivalent thereof may be administered in a convenient manner such as by the oral, intravenous (where water soluble), intraperitoneal, intramuscular, subcutaneous, intradermal or suppository routes or implanting (e.g. using slow release molecules). With particular reference to use of the agent and neuronal tracer complex, the complex may be administered in the form of pharmaceutically acceptable nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder such as tragacanth, corn starch or gelatin; a disintegrating agent, such as alginic acid; and a lubricant, such as magnesium stearate.

In yet another aspect of the present invention relates to the use of a composition comprising an agent capable of modulating neuronal cell activity linked, fused or otherwise associated with a neuronal tracer in the manufacture of a medicament for the modulation of neuronal cell activity in a subject.

Preferably the neuronal tracer is a retrograde neuronal tracer. Still more preferably the modulation of neuronal cellular activity is induction of neuronal cell apoptosis and the agent is a neurotoxin such as saporin.

Another aspect of the present invention provides a composition for use in modulating the cellular activity of a neuron comprising an agent linked fused or otherwise associated with a neuronal tracer and one or more pharmaceutically acceptable carriers and/or diluents.

Preferably the neuronal tracer is a retrograde neuronal tracer. Still more preferably the modulation of neuronal cellular activity is induction of neuronal cell apoptosis.

Compositions suitable for injectable use include sterile aqueous solutions (where water soluble) and sterile powders for the extemporaneous preparation for sterile injectable solutions. They are preferably stable under the conditions of manufacture and storage and are preferably preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof and vegetable oils. The prevention of the action of microorganisms can be brought about by various antibacterial and antifungal agents, for example, parabens, chlorobutanol, phenol, sorbic acid, thirmerosal and the like. In many cases, it will preferable to include isotonic agents, for example, sugars or sodium chloride. Prolonged absorption of the injectable compositions can be brought about by the use in the compositions of agents delaying absorption, for example, aluminum monostearate and gelatin.

Such injectable solutions are prepared by incorporating the active compounds in the required amount in the appropriate solvent with various of the other ingredients enumerated above, as required, followed by, for example, filter sterilization or sterilization by other appropriate means. Dispersions are also contemplated and these may be prepared by incorporating the various sterilized active ingredients into a sterile vehicle which contains the basic dispersion medium and the required other ingredients from those enumerated above. In the case of sterile powders for the preparation of sterile injectable solutions, a preferred method of preparation includes vacuum drying and the freeze-drying technique which yield a powder of the active ingredient plus any additional desired ingredient from a previously sterile-filtered solution.

When the active ingredients are suitably protected, they may be orally administered, for example, with an inert diluent or with an assimilable edible carrier, or it may be enclosed in hard or soft shell gelatin capsule, or it may be compressed into tablets. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparation may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 ng and 2000 mg of active compound.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Any material used in preparing any dosage unit form should be pharmaceutically pure and substantially non-toxic in the amounts employed. In addition, the active compound(s) may be incorporated into sustained-release preparations and formulations.

The present invention also extends to forms suitable for topical applications such as creams, lotions and gels. In such forms, agent/tracer may need to be modified to permit penetration of the surface barrier.

Pharmaceutically acceptable carriers and/or diluents include any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved and (b) the limitations inherent in the art of compounding such an active material to induce or facilitating analgesia in living subjects.

Effective amounts of the composition contemplated by the present invention will vary depending on the severity of the pain and the health and age of the recipient. In general terms, effective amounts may vary from 0.01 ng/kg body weight to about 100 mg/kg body weight. Alternative amounts include for about 0.1 ng/kg body weight about 100 mg/kg body weight or from 1.0 ng/kg body weight to about 80 mg/kg body weight.

Further features of the present invention are more fully described in the following examples. It is to be understood, however, that this detailed description is included solely for the purpose of exemplifying the present invention. It should not be understood in any way as a restriction on the broad description of the invention as set out above.

EXAMPLES

Example 1

Preparation of CTB-Saporin

A conjugate of cholera toxin B subunit (CTB) and saporin was prepared utilizing a published procedure to couple the two compounds through a reducible disulfide linkage. Saporin was isolated from the seeds of *Saponaria officinalis*.

Injection of CTB-Saporin

Male Sprague-Dawley rats weighing 250–350 g were anesthetised with sodium pentobarbitone (60 mg/kg). Five microlitres of a 1% solution of CTB-saporin prepared as described above were injected into the right superior cervical ganglion.

Tissue Processing

Three, seven or fourteen days after the injection of CTB-saporin, rats were re-anaesthetized with sodium pentobarbitone (60 mg/kg). Heparin (1000–5000 IU) was injected into the heart and the animals were perfused with 150–200 ml of tissue culture medium (DMEM/Ham's F12; Sigma D-8900) followed by 1 L of 4% formaldehyde in 0.1M phosphate buffer, pH 7.4. Spinal cords were removed; spinal cord segment T1 was identified by the position of its root caudal to the first rib and marked. The cords were post-fixed intact for 3 days at room temperature on a shaker. After cords had been post-fixed and washed several times in phosphate buffer, blocks were made of thoracic segments T1–T4. The rostral border of the dorsal root entry zone was taken as the rostral boundary for each segment and marked with a cut. The blocks were then sectioned longitudinally on a Vibratome at 50 $\mu$m.

The Vibratome sections were washed several times in phosphate buffer, treated with 50% ethanol in distilled water for 30 min [Llewellyn-Smith I J et al., *J. Histochem. Cytochem.*, 40:1741–1749 (1992)], washed again in phosphate buffer and then exposed to 10% normal horse serum (NHS) diluted with 10 mM Tris, 0.9% NaCl, 0.05% thimerosal (Sigma T-5125) in 10 mM sodium phosphate buffer (TPBS) for 30 min. The sections were then incubated for 2 days in a goat antiserum against choline acetyltransferase (ChAT; Chemicon) diluted 1:5,000 with TPBS containing 10% NHS. This dilution was determined by titration to give the maximum number of immunoreactive spinal neurons with the minimum level of non-specific background staining. The sections were subsequently incubated for 24 hrs in biotinylated donkey anti-sheep immunoglobulin (Sigma) diluted 1:200 in TPBS containing 1% NHS followed and then overnight in a 1:1500 dilution of ExtrAvidin-horseradish peroxidase (Sigma E-2886) in TPBS. All steps were carried out at room temperature on a shaker and sections were washed 3×30 min in TPBS after each incubation. ChAT-immunoreactive sympathetic preganglionic neurons (SPN) were revealed by a nickel-intensified diaminobenzidine reaction in which peroxide was generated by glucose oxidase [Llewellyn-Smith I J, Pilowsky P., *J. Neurosci. Methods,* 46:27–40 (1993)]. After several washes in phosphate buffer, sections were air-dried onto chrome alum slides, defatted in chloroform and acetone, cleared with xylene and mounted in DePeX.

Quantification

Since SPN projecting to the superior cervical ganglion are concentrated in the most rostral thoracic spinal cord segments [Strack A M, Sawyer et al., *Brain Res.,* 455:187–191 (1988)], ChAT-immunoreactive neurons in the internediolateral cell column (IML) were quantified in segments caudal T1, T2 and T3 of all animals. Neurons belonging to the IML are difficult to distinguish in rostral T1 because they are not clumped so neurons in this region were not quantified. Only neurons containing complete nuclear profiles were included in the counts. The number of ChAT-immunoreactive SPN ipsilateral to the injection site was compared to the number of the contralateral side.

Example 2

Results

By three days after injection of the toxin-tracer into the superior cervical ganglion, according to the method described in Example 1, many SPN in the IML died as a result of retrograde transport of CTB-saporin. In caudal T1 to T3, the number of ChAT-immunoreactive neurons in the IML ipsilateral to the injection site had been reduced to about 50% of the number on the contralateral side. SPN continued to disappear from the IML between 3 days and 7 days, by which time the ipsilateral IML contained only about 40% of the neurons present on the contralateral side. The decline in SPN number continued between 7 and 14 days so that, after 2 weeks, about 70–80% of the neurons in the IML in the most rostral thoracic segments were dead (Tables 1–11).

Rat #C255

| TABLE 1 | CS/Rost T1 | | Caud T1 | | T2 | | T3 | | TOTAL | |
|---|---|---|---|---|---|---|---|---|---|---|
| | No. | % | No. | % | No. | % | No. | % | No. | % |
| RHS | N/A | | 178 | 37.5 | 191 | 45.6 | 397 | 88.2 | 786 | 56.1 |
| LHS | N/A | | 475 | 100 | 393 | 100 | 450 | 100 | 1318 | 100 |
| Total Neurons | | | 653 | | 584 | | 847 | | 2084 | |

Rat #C256

| TABLE 2 | CS/Rost T1 | | Caud T1 | | T2 | | T3 | | TOTAL | |
|---|---|---|---|---|---|---|---|---|---|---|
| | No. | % | No. | % | No. | % | No. | % | No. | % |
| RHS | N/A | | 86 | 19.8 | 280 | 52.0 | 421 | 75.2 | 787 | 51.4 |
| LHS | N/A | | 434 | 100 | 538 | 100 | 560 | 100 | 1532 | 100 |
| Total Neurons | | | 520 | | 818 | | 981 | | 2319 | |

Rat #C257

| TABLE 3 | CS/Rost T1 | | Caud T1 | | T2 | | T3 | | TOTAL | |
|---|---|---|---|---|---|---|---|---|---|---|
| | No. | % | No. | % | No. | % | No. | % | No. | % |
| RHS | N/A | | 137 | 53.9 | 470 | 69.9 | 341 | 76.5 | 948 | 69.1 |
| LHS | N/A | | 254 | 100 | 672 | 100 | 445 | 100 | 1371 | 100 |
| Total Neurons | | | 391 | | 1142 | | 786 | | 2319 | |

Rat #C268

| TABLE 4 | CS/Rost T1 | | Caud T1 | | T2 | | T3 | | TOTAL | |
|---|---|---|---|---|---|---|---|---|---|---|
| | No. | % | No. | % | No. | % | No. | % | No. | % |
| RHS | N/A | | 101 | 27.7 | 111 | 36.8 | 152 | 56.1 | 364 | 38.9 |
| LHS | N/A | | 364 | 100.0 | 302 | 100.0 | 271 | 100.0 | 937 | 100.0 |
| Total Neurons | | | 465 | | 413 | | 423 | | 1301 | |

Rat #C249

| TABLE 5 | CS/Rost T1 | | Caud T1 | | T2 | | T3 | | TOTAL | |
|---|---|---|---|---|---|---|---|---|---|---|
| | No. | % | No. | % | No. | % | No. | % | No. | % |
| RHS | N/A | | 71 | 18.5 | 236 | 41.8 | 286 | 58.7 | 593 | 41.3 |
| LHS | N/A | | 383 | 100 | 565 | 100 | 487 | 100 | 1435 | 100 |
| Total Neurons | | | 454 | | 801 | | 773 | | 2028 | |

Rat #C250

| TABLE 6 | CS/Rost T1 | | Caud T1 | | T2 | | T3 | | TOTAL | |
|---|---|---|---|---|---|---|---|---|---|---|
| | No. | % | No. | % | No. | % | No. | % | No. | % |
| RHS | N/A | | 96 | 21.1 | 180 | 37.8 | 243 | 61.4 | 519 | 39.1 |
| LHS | N/A | | 456 | 100 | 476 | 100 | 396 | 100 | 1328 | 100 |
| Total Neurons | | | 552 | | 656 | | 639 | | 1847 | |

Rat #C251

| TABLE 7 | CS/Rost T1 | | Caud T1 | | T2 | | T3 | | TOTAL | |
|---|---|---|---|---|---|---|---|---|---|---|
| | No. | % | No. | % | No. | % | No. | % | No. | % |
| RHS | N/A | | 79 | 23.4 | 159 | 33.4 | 177 | 52.8 | 415 | 36.1 |
| LHS | N/A | | 337 | 100 | 476 | 100 | 335 | 100 | 1148 | 100 |
| Total Neurons | | | 416 | | 635 | | 512 | | 1563 | |

Rat #C267

| TABLE 8 | CS/Rost T1 | | Caud T1 | | T2 | | T3 | | TOTAL | |
|---|---|---|---|---|---|---|---|---|---|---|
| | No. | % | No. | % | No. | % | No. | % | No. | % |
| RHS | N/A | | 42 | 9.9 | 134 | 38.2 | 295 | 79.9 | 471 | 41.2 |
| LHS | N/A | | 423 | 100 | 351 | 100 | 369 | 100 | 1143 | 100 |
| Total Neurons | | | 465 | | 485 | | 664 | | 1614 | |

TABLE 9: Rat #C252

|  | CS/Rost T1 | | Caud T1 | | T2 | | T3 | | TOTAL | |
|---|---|---|---|---|---|---|---|---|---|---|
|  | No. | % | No. | % | No. | % | No. | % | No. | % |
| RHS | N/A | | 59 | 19.3 | 85 | 15.5 | 119 | 41.5 | 263 | 23.0 |
| LRS | N/A | | 306 | 100 | 548 | 100 | 287 | 100 | 1141 | 100 |
| Total Neurons | | | 365 | | 633 | | 406 | | 1404 | |

TABLE 10: Rat #C253

|  | CS/Rost T1 | | Caud T1 | | T2 | | T3 | | TOTAL | |
|---|---|---|---|---|---|---|---|---|---|---|
|  | No. | % | No. | % | No. | % | No. | % | No. | % |
| RHS | N/A | | 41 | 7.8 | 115 | 23.7 | 187 | 50.4 | 343 | 24.9 |
| LHS | N/A | | 523 | 100 | 485 | 100 | 371 | 100 | 1379 | 100 |
| Total Neurons | | | 564 | | 600 | | 558 | | 1722 | |

TABLE 11: Rat #C266

|  | CS/Rost T1 | | Caud T1 | | T2 | | T3 | | TOTAL | |
|---|---|---|---|---|---|---|---|---|---|---|
|  | No. | % | No. | % | No. | % | No. | % | No. | % |
| RHS | N/A | | 40 | 15.1 | 79 | 23.0 | 137 | 50.6 | 256 | 29.1 |
| LHS | N/A | | 265 | 100.0 | 343 | 100.0 | 271 | 100.0 | 879 | 100.0 |
| Total Neurons | | | 305 | | 422 | | 408 | | 1135 | |

In some embodiments, CTB-saporin may be particularly advantageous for modulation of sympathetic preganglionic neurons, large diameter myelinated sensory neurons and motor neurons. Isolectin B4-saporin may be particularly advantageous for modulation of small diameter unmyelinated neurons. And, wheat germ agglutinin-saporin may be particularly advantageous for modulation of small unmyelinated sensory neurons and small to medium lightly myelinated neurons.

From the foregoing detailed description and examples, it will be evident that modifications and variations can be made to the compositions and methods of the invention without departing from the spirit of the scope of the invention. Therefore, it is intended that all modifications and verifications not departing from the spirit of the invention come within the scope of the claims and their equivalents.

What is claimed is:

1. A method of inducing neuron apoptosis in a live subject, said method comprising peripherally a ministering to said live subject an effective amount of an agent associated with a neuronal tracer, wherein said neuronal tracer is selected form the group consisting of cholera toxin B subunit, wheat germ agglutinin, and isolectin B4 from *Bandeireaea simplicifolia,* wherein said neuronal tracer associates with a neuron and facilitates transportation of said agent to a cell body of said neuron for said agent to induce apoptosis in said neuron.

2. A method according to claim 1 wherein said neuronal tracer is a retrograde neuronal tracer.

3. A method according to claim 2 wherein said retrograde neuronal tracer is selected from the group consisting of cholera toxin B subunit, wheat germ agglutinin, and isolectin B4.

4. A method according to claim 2 wherein said agent is a neurotoxin.

5. A method according to claim 4 wherein said neurotoxin is a ribosomal inactivating protein.

6. A method according to claim 5 wherein said ribosomal inactivating protein is selected from the group consisting of abrin, saporin and modeccin.

7. A method of delivering to a cell body of a neuron an agent for inducing neuron apoptosis in a live subject said method comprising peripherally administering to said live subject an effective amount of an agent for inducing neuron apoptosis said agent being associated with a neuronal tracer, wherein said neuronal tracer is selected form the group consisting of cholera toxin B subunit, wheat germ agglutinin, and isolectin B4 from *Bandeireaea simplicifolia*, wherein said neuronal tracer associates with said neuron and facilitates transportation of said agent to the cell body of said neuron to induce apoptosis in said neuron.

8. A method according to claim 7 wherein said neuronal tracer is a retrograde neuronal tracer.

9. A method according to claim 8 wherein said retrograde neuronal tracer is selected from the group consisting of cholera toxin B subunit, wheat germ agglutinin, and isolectin B4.

10. A method according to claim 8 wherein said agent is a neurotoxin.

11. A method according to claim 10 wherein said neurotoxin is a ribosomal inactivating protein.

12. A method according to claim 11 wherein said ribosomal inactivating protein is selected from the group consisting of abrin, saporin, and modeccin.

13. A method of treating involuntary muscles spasms or chronic pain in a live subject said method comprising peripherally administering to said live subject an effective amount of an agent associated with a neuronal tracer for a time and under conditions sufficient for said neuronal tracer to associate with a neuron and facilitate transportation of said agent to the cell body of said neuron to induce neuron apoptosis, wherein said tracer is selected form the group consisting of cholera toxin B subunit, wheat germ agglutinin, and isolectin B4 from *Bandeireaea simplicifolia*.

* * * * *

UNITED STATES PATENT AND TRADEMARK OFFICE
CERTIFICATE OF CORRECTION

PATENT NO.    : 6,376,460 B2
DATED         : April 23, 2002
INVENTOR(S)   : Llewellyn-Smith It is certified that error appears in the above-identified patent and that said Letters Patent is hereby corrected as shown below:

Column 17,
Line 57, "peripherally a ministering" should read -- peripherally administering --

Column 18,
Line 54, "form" should read -- from --

Signed and Sealed this

Thirty-first Day of December, 2002

JAMES E. ROGAN
*Director of the United States Patent and Trademark Office*